United States Patent [19]

Carter

[11] Patent Number: 5,803,934
[45] Date of Patent: Sep. 8, 1998

[54] METHOD OF PRODUCING AN ELECTRODE LAYER ON A SOLID OXIDE ELECTROLYTE OF A SOLID STATE FUEL CELL

[75] Inventor: John David Carter, Roskilde, Denmark

[73] Assignee: Forskningscenter RISØ, Roskilde, Denmark

[21] Appl. No.: 596,314

[22] PCT Filed: Aug. 12, 1994

[86] PCT No.: PCT/DK94/00304

§ 371 Date: Feb. 20, 1996

§ 102(e) Date: Feb. 20, 1996

[87] PCT Pub. No.: WO95/05685

PCT Pub. Date: Feb. 23, 1995

[30] Foreign Application Priority Data

Aug. 18, 1993 [DK] Denmark ................................. 0943/93

[51] Int. Cl.[6] ...................................................... H01M 6/00

[52] U.S. Cl. ........................................... 29/623.5; 29/623.1

[58] Field of Search ................................ 429/33, 40, 218, 429/59, 101; 29/623.1, 623.5; 427/77, 115

Primary Examiner—Bruce F. Bell
Attorney, Agent, or Firm—Hill, Steadman & Simpson

[57] ABSTRACT

Vanadium doping has been found to increase the sinterability of $La_xCa_yCrO_3$ (x+y=1) while retaining its high temperature electrical and chemical properties. Specimens of $La_xCa_yCrO_3$ with about 2 mol % V were sintered at 1,300° to 1,450° C. for 2 to 8 hours to achieve more than 92% theoretical density, as compared to less than 75% for those specimens not containing V. The electrical conductivity of $La_{0.76}Ca_{0.26}CrO_3$+2 mol % V in $10^{-16}$ and 1 atm of $O_2$, was measured to be 12 and 30 S/cm, respectively. Preliminary experiments with tape cast laminates and spray coated specimens give indication that $La_xCa_yCrO_3$+V can be sintered on YSZ with good adherence between the two materials.

14 Claims, 8 Drawing Sheets

METHOD OF PRODUCING AN ELECTRODE LAYER ON A SOLID OXIDE ELECTROLYTE OF A SOLID STATE FUEL CELL

BACKGROUND OF THE INVENTION

1. Field of the Invention

This is a 371 of PCT/DK94/00304 filed on Aug. 08, 1994.

The present invention relates to a method of producing an electrode layer on, for instance, a solid electrolyte of a solid state fuel cell, where the electrode material is of the type $La_xCa_yCrO_3$, and $X+Y \geq 1$ and $Y>0$, the electrode material being subjected to a sintering.

2. Description of the Related Art

The sintering must be as efficient as possible. In addition, it must be possible to carry out cosintering with other materials, such as YSZ. The sinterings were originally carried out at relatively high temperatures. It was discovered that it was possible to lower the temperature by adding La and Ca in excess to the composition, whereby the fluid and spreading characteristics of an intrinsic wet phase and consequently the densification are improved. However, the resulting stability may be deteriorated, and the excess ingredients may react with the adjacent materials which presents a drawback for instance in connection with SOFC (Solid oxide fuel cell) cells.

SUMMARY OF THE INVENTION

An object of the invention is to provide a method of producing all electrode material with improved sintering properties, the risk of reactions with the adjacent materials simultaneously being reduced or eliminated.

The method according to the invention is characterised by adding a few mol %, preferably 1 10 mol %, of vanadium to the electrode material, whereby the resulting densities turned out to be considerably improved. A cosintering with YSZ indicates that it is possible to cosiniter with YSZ without involving reactions with YSZ.

According to the invention it is particularly advantageous to add 1 to 2 mol % of vanadium, whereby the density can be increased to 96%.

The method according to the invention may for instance be used for producing a heat resistance.

As an alternative, the method according to the invention can be used for producing a sensor electrode, such as an oxygen sensor electrode.

DETAILED DESCRIPTION OF THE PREFERRED EMBODIMENTS

A ceramic $La_xCa_yCrO_3$ can be used as an electric conductor at high temperatures. The electrical conductivity thereof at 1,000° C. is 5 to 50 S/cm at an oxygen partial pressure $P_{O_2}$ of $10^{-18}$ to 1 atm. This material can be used as a heating unit in an oven, as connectors and anodes in SOFC, and as electrodes for zirconia-based $O_2$ sensors.

One of the greatest challenges of using $La_xCa_yCrO_3$ is to sinter in air at moderate temperatures of less than 1,500° C. Chromium oxides ($CrO_\delta$, where $\delta=2$ to 3) volatilize from $La_xCa_yCrO_3$ and result in concentrating particle coarsening mechanisms. Alkaline earth doped $LaCrO_3$ was originally sintered at 1,700° C. in a reducing atmosphere ($P_{O_2}=10^{-11}$ atm) to lower the vapour pressure of $CrO_\delta$. This method provided densities of more than 95% of the theoretically possible densities.

Later it was found that such densities could be achieved in air at 1,300° to 1,500° C. by synthesizing $La_xCa_yCrO_3$ with $y \geq 0.25$ and $x+y>1$ or by creating an excess of A sites, reference being made to the crystal structure of $ABO_3$ perovskite. Such compositions release extra Ca into a temporarily exsolved liquid phase $Ca_{1+\delta}$—$CrO_4$ used for promoting the sintering. The ability of the $Ca_{1+\delta}CrO_4$ to promote a sintering is increased with an increasing excess of A site ions. The densification proceeds as a consequence of a mass transport of the ingredients through the liquid, which promotes the grain growth and the filling of intergranular pores. By the achievement of high densities it is assumed that $Ca_{1+\delta}CrO_4$ is redissolved into $La_xCa_yCrO_3$ to form a single phase solid solution.

Some problems arise by this sintering method. It is also difficult to form a solid solution with $La_xCa_yCrO_3$ by substituting Ca for La in excess of 25 mol %. Thus, the $Ca_{1+\delta}CrO_4$ is reactive towards corresponding materials during sintering and subsequent heating cycles. Secondary phases develop from interfacial reactions which are less chemically stable and have lower electric conductivities. These ultimately degrade the desired properties of $La_xCa_yCrO_3$.

These problems can be minimized by reducing the total amount of Ca substituted into $La_xCa_yCrO_3$ to less than 25% and by keeping the excess of A sites near the stoichiometric limit (i.e. $x+y \approx 1$). When these precautions have been taken, the sinterability of $La_xCa_yCrO_3$ is reduced and it is again difficult to obtain a high density.

A demand exists therefore, for a method of reducing the calcium reactivity while maintaining a high sinterability together with the chemical and electrical properties of $La_xCa_yCrO_3$. By adding V to $La_xCa_yCrO_3$, the sinterability thereof is improved without requiring an excess of A site cations or an excess of Ca. The chemical stability and the electrical properties and a low V doping (of <5 mol %) have been found to be similar to undoped $La_xCa_yCrO_3$.

Powder compositions were prepared by two different processes. Both are polymer pyrolysis techniques including a dissolving of metal nitrates in water and an adding of chelating agents to form a polymer precursor. Water is evaporated from the precursor solution to form a gel and the gel is pyrolysed to remove organic ingredients, which results in a homogenous mixture of metal oxides.

The liquid mixture process (LM) uses ethylene glycol and citric acid as chelating agents, cf. L. Tai, P. Lessing "Modified resin-intermediate processing of perovskite powders: Part II. Processing for fine, nonagglomerated Sr-doped lanthanum chromite powders", J. Mater. Res., 7 [2], 511–519 (1992). The pyrolysis occurs at a slow rate (for 1 to 3 hours) and at low temperatures of about 300° C. This technique was chosen so that V could be added into the initial synthesis of $La_xCa_yCrO_3$ without risking a volatilization during the polymer pyrolysis.

Standardized aqueous solutions of La, Ca, and Cr nitrates were mixed in a glass beaker with ethylene glycol and citric acid so that the molar ratios of the final $La_xCa_yCrO_3$ composition/ethylene glycol/citric acid=1:1:1.

Vanadium oxide $V_2O_5$ of a purity of 99.9% was used as V-source. Since the pentaoxide is difficult to dissolve in an aqueous solution, a soluble $VO_\delta$-citric acid complex was prepared by mixing $V_2O_5$ and citric acid in deionized water with a weight ratio of oxide to acid to water of 1:4:20 and by heating to 80° to 90° C. The complex reaction was completed at the formation of a clear blue solution. This colour is an indication of oxovanadium (the IV-compound, cf. F. A. Cotton and G. W. Wilkinson advanced inorganic chemistry a comprehensive text. Interscience Publishers, New York 1972 p 825), although the structure of the $VO_\delta$-citric acid complex has not been determined. This solution was added to the solution of chelated La, Ca, and Cr ions or used as a coating as described below.

The LM solution containing the $VO_{67}$-citric acid complex was heated on a hot plate to about 80° C. to remove water and to form a polymeric gel. After the formation of the gel, the temperature of the hot plate was raised to about 300° C., and the gel was polymerized in an amorphous char. The charge was ball milled in ethanol for 4 hours, dried and calcined at 750° C. for 4 hours to obtain a crystalline phase and to remove residual carbon.

The Glycine process is described by L. A. Chick, J. L. Bates, L. R. Pederson and H. E. Kissinger in the paper "Synthesis of Air-Sinterable Lanthanum Chromite Powders", p 170–187, in *Proceedings of the First International Symposium on Solid Oxide Fuel Cells,* vol. 89-11, edited by S. C. Singhal (Pennington N.J.: The Electrochemical Society, Inc. 1989). This process uses glycine as a chelating agent and a fuel for pyrolysis. The pyrolysis occurs in 2 to 3 sec and at temperatures exceeding 1,000° C. The powder resulting from this process is crystalline, nanometer sized (~50 nm), weakly agglomerated and free of organic residues. The amount of glycine used is determined by the amount of nitrate in the solution and the amount of metals which must be chelated. A glycine:nitrate ratio G:N is first calculated to obtain the most efficient combustion. By way of tests it was determined that a G:M ratio of at least 1.5 is needed to chelate all the metals. Extra glycine and $HNO_3$ can be added to the solution to satisfy both requirements. At the proper value G:N, a vigorous reaction occurs which obtains peak flame temperatures of >1,000° C. Since $VO_2$ and $V_2O_5$ have high vapour pressures at these temperatures, it was speculated that V might be lost during the synthesis. $La_xCa_yCrO_3$ was consequently synthesized with and without V to determine the difference in the sinterability. Aqueous La, Ca, and Cr nitrate solutions, the $VO_\delta$-citric acid complex, and glycine were balanced in a tall 2,000 ml beaker, where G:N=0.5 and G:M=1.5 to 1.7. A 40 mesh screen of steel was placed over the top of the beaker to capture fine solid particles during the pyrolysis. The batch size should not exceed 0.05 mol of perovskite to contain the powder in the beaker during the pyrolysis. The mixture was heated in a fume hood to remove water, being careful not to exceed 200° C. to avoid premature ignition. After formation of a syrupy gel, the solution was heated to 300° C. and pyrolysed. After pyrolysis, the powder was subjected to a dry ball milling to break up agglomerates and calcined into air as specified in Table I to coarsen the powders.

Calcined powder not synthesized with V was coated with the $VO_\delta$-citric acid solution. The solution was added in desired doping amounts to a slurry of $La_xCa_yCrO_3$ in ethanol.

After a suitable mixing, the slurry was dried and recalcined at 500° to 600° C. to remove organic substances.

Specimens were formed by uniaxially pressing powders into disks or bars at 150 to 200 MPa. Sintering temperatures and times are summarized in Table I.

The electrical conductivity was measured for $La_{0.76}Ca_{0.24}CrV_{0.02}O_3$ at 1,000° C. in air and at $10^{-16}$ atm $O_2$ using a four point measuring technique described by H. Toftegaard and M. Mogensen in the paper "Electrical Conductivity of LSM", unpublished departmental report: BC-103, Risø National Laboratory, Roskilde DK, December 1992. The current source is specially designed, and the device for measuring the electrical voltages was a HP3421A data acquisition and control unit.

Manually cast foils were made from the composition $La_{0.76}Ca_{0.26}CrO_3$+2 mol % V. Powder slurries were prepared and cast on a glass substrate into a tape of 9·60·0.03 cm, using a tape casting technique developed by Risø, cf. the paper by C. Bagger "Improved Production Methods for YSZ Electrolyte and Ni—YSZ Anode for SOFC" Extended abstract of poster, presented at the 1992 Fuel Cell Seminar, Tucson, Ariz., Nov. 29 to Dec. 2, 1992. The chromate tapes were laminated with a green 8 mol % YSZ tape by painting and corresponding surfaces of the tapes with ethanol by passing the laminates through a roller mill. The laminates were placed between fibrous alumina plates to prevent curling and sintered in air at 1,300° C. for 6 hours.

A spray coating slurry was prepared containing 12% by weight of $La_{0.8}Ca_{0.2}Cr_{0.98}V_{0.02}O_3$ (calcined at 1,000° C. for 2 hours), 12% by weight "as synthesized" powder (from the same batch), 56% by weight of ethanol, 4% by weight of polyvinyl pyrrolidone solution (PVP) [0.53 g PVP/g 66% by volume of methylethylketone, 33% by volume of ethanol], and 16% by weight of 3 mol % $Y_2O_3$ partially stabilized ytterbium (TZ-3Y from Tosoh Corp. Tokyo 170, Japan) (PSZ). The first three ingredients and half the PVP were ball milled for 24 hours. PSZ and the remaining PVP were then added to the slurry, and the entire mixture was again ball milled for 24 hours. After milling, the slurry was sprayed onto sintered YSZ tapes with an airbrush and dried for 15 minutes. The coated YSZ plates were then sintered at 1,300° C. for two hours.

TABLE I

Sintering data for $La_xCa_yCrO_3$ + V

| $La_xCa_y$-$CrO_3$ + V Composition | Powder Synthesis Calcination Conditions and V Addition Method | Sintering temp/time | Density (g/cm³) | Theoretical Density |
|---|---|---|---|---|
| $La_{0.76}$-$Ca_{0.26}C$-$rO_3$ | Glycine-1200° C./2 h | 1350° C. /3 h | 4.45 | 72% |
| *$La_{0.76}$-$Ca_{0.26}C$-$rO_3$ + 2 mol % V | Glycine-1200° C./2 h $VO_\delta$-citric acid coated | 1300° C. /2 h | 6.02 | 96% |
| $La_{0.76}$ $Ca_{0.24}$-$CrV_{0.02}O_3$ | LM-750° C./4 h V doped | 1300° C. /2 h | 5.68 | 91% |

TABLE I-continued

Sintering data for $La_xCa_yCrO_3 + V$

| $La_xCa_y$-$CrO_3 + V$ Composition | Powder Synthesis Calcination Conditions and V Addition Method | Sintering temp/time | Density (g/cm³) | Theoretical Density |
|---|---|---|---|---|
| $La_{0.8}Ca_{0.2}CrO_3$ | Glycine-1200° C./2 h | 1450° C. /8 h | 4.37 | 69% |
| $La_{0.8}Ca_{0.2}CrO_3$ + 1 mol % V | Glycine-1200° C./2 h $VO_x$-citric acid coated | 1450° C. /8 h | 5.85 | 92% |
| *$La_{0.8}$-$Ca_{0.2}Cr_{0.98}V_{0.02}O_3$ | Glycine-1000° C./8 h V doped | 1450° C. /8 h | 5.95 | 94% |
| $La_{0.8}Ca_{0.2}Cr_{0.95}V_{0.10}O_3$ | Glycine-1000° C./2 h V doped | 1350° C. /2 h | 5.96 | 94% |

The sintering densities are summarized in Table I. In general, the sintering density of $La_xCa_yCrO_3$ has been improved from less than 75% to more than 90% of the theoretical value by the addition of V. The temperature and the necessary times needed to obtain a high density depend on the total amount of Ca added to the V doped composition. Ca additions of 24 to 26 mol % required 1,300° C. and 2 hours for achieving high densities, whereas additions of 20 mol % Ca required 1,450° C. and 8 hours. The temperature and the time were, however, reduced to 1,350° C. and 2 hours for the 20 mol % Ca composition when the V content was increased to a total of 10 mol % with an excess of 5 mol %.

The compositions indicated by a * are stoichiometric with respect to the A and B cations (i.e. A/B=1). It is assumed that V substitutes on the B site since $V^{3+}$ and $V^{4+}$ have ionic radii similar to $Cr^{3+}$ and $Cr^{4+}$. This is the major advantage of adding V to $La_xCa_yCrO_3$. Previous low temperature sintering compositions of $La_xCa_yCrO_3$ required an excess of A cations (x+y>1) to achieve high sintering densities. Stoichiometric $La_xCa_yCrO_3$ is preferred because the reactivity of Ca in the liquid phase is reduced and a single phase is obtained after sintering.

The sinterability of powders prepared by means of LM, glycine or $VO_x$-citric acid coating processes are all comparable. Apparently, V does not evaporate at high temperatures as was supposed, but it is incorporated in the $La_xCa_yCrO_3$ system. Vanadium can therefore be added to $La_xCa_yCrO_3$ at various stages of powder synthesis and can even be used to balance the stoichiometry in existing $La_xCa_yCrO_3$ powders.

Table II shows the electrical conductivity values of $La_{0.76}Ca_{0.24}CrV_{0.01}O_3$ at 100° C. in air and under reducing conditions. These values lie within the conductivity range of similar $La_xCa_yCrVO_3$ compositions developed by Risø.

TABLE II

Electrical conductivities of $La_{0.76}Ca_{0.24}CrV_{0.01}O_3$ at 100° C.

| Atmospheric gases/Po₂ (atm) | Conductivity (S/cm) |
|---|---|
| air/0.21 | 30 |
| 9%H₂,3%H₂O,91%N₂/3.2 × 10⁻¹⁶ | 12 |

Laminates of $La_{0.76}Ca_{0.26}CrO_3$+2 mol % V and /YSZ demonstrated good bonding at their interface after sintering. The $La_{0.80}Ca_{0.20}Cr_{0.98}V_{0.02}O_3$-PSZ spray coated mixture showed good adherence to the YSZ surface. These preliminary tests indicate that $La_xCa_yCrO_3$ can be attached to YSZ by way of cosintering and are used to form electrodes or interconnectors for SOFC and in connection with YSZ oxygen sensors.

Thus, vanadium additions of 1 to 2 mol % have shown to significantly improve the sinterability of $La_xCa_yCrO_3$ without requiring the addition of an excess of A site cations or of extra Ca. The electrical conductivity of V-doped $La_xCa_yCrO_3$ was unchanged compared to undoped compositions. Preliminary tests indicate the possibility of bonding $La_xCa_yCrO_3$ to YSZ by cosintering or spray coating techniques. It is believed that an addition of V can further improve the sinterability of other rare-earth/chromium based materials such as $Y_xCa_yCrO_3$, $LaCr_xMg_yO_3$, and $La_xSr_yCrO_3$.

Additional investigation into the $(La,M)(Cr,V)O_3$ perovskite system has sought to gain a better understanding of the effect of V as a sintering aid. More $(La,Ca)(Cr,V)O_3$ and $(La,Sr)(Cr,V)O_3$ batches were synthesized and sintered to further verify the effect of V on the sinterability of these systems. Microscopic and phase analyses show that a liquid phase forms which is based on the $CaO—Cr_2O_3$ phase system for $(La,Ca)CrO_3$ compositions. This liquid is found to contain V and it is believed that the V modifies the sintering characteristics. A similar liquid was observed in the $(La,Sr)CrO_3$ compositions based on $SrCrO_4$ from the $SrO—Cr_2O_3$ phase system.

Additional electrical measurements show that the addition of V has little effect on the conductivity of $(La,M)CrO_3$ (M= Ca,Sr) in air or under a reducting atmosphere.

Microscopic analysis (La,Ca) (Cr,V)O₃

Figure 1:
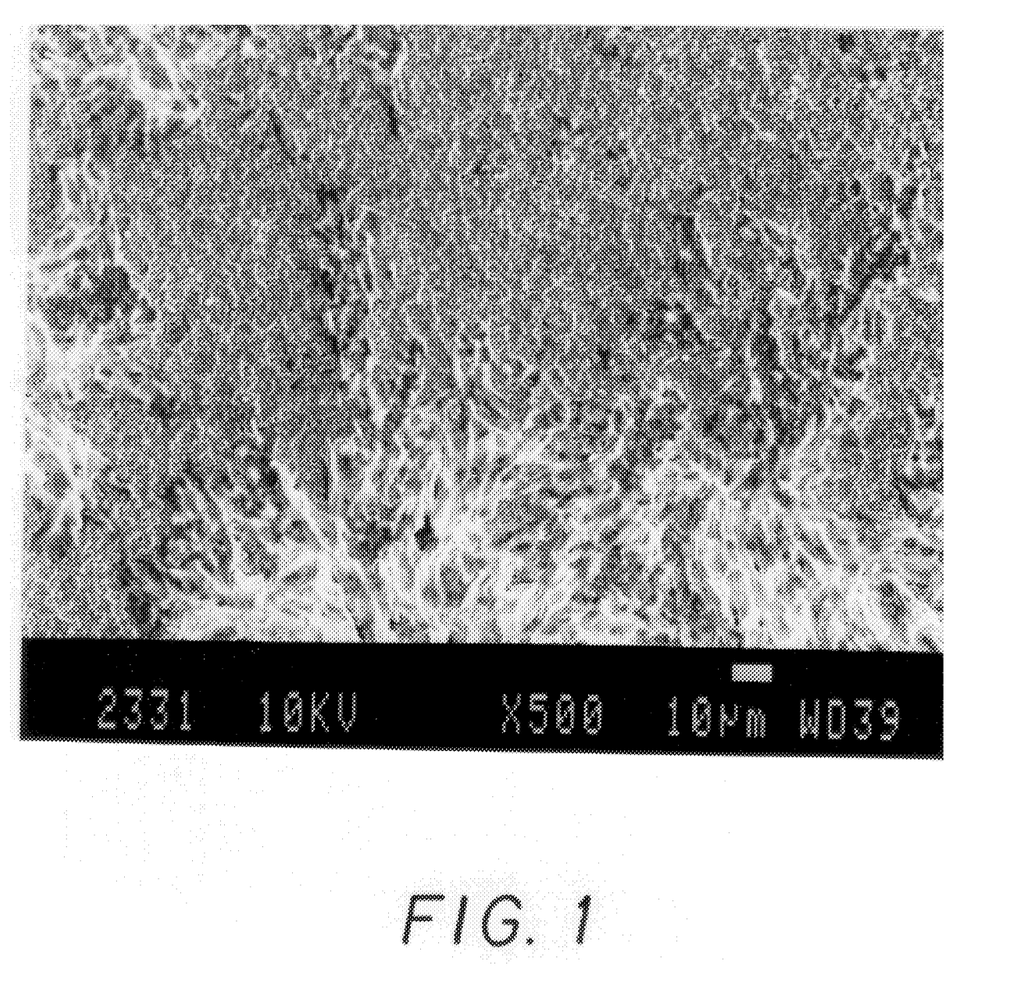
FIG. 1 is a photograph of an unpolished surface of a material according to the present invention.
Figure 2:
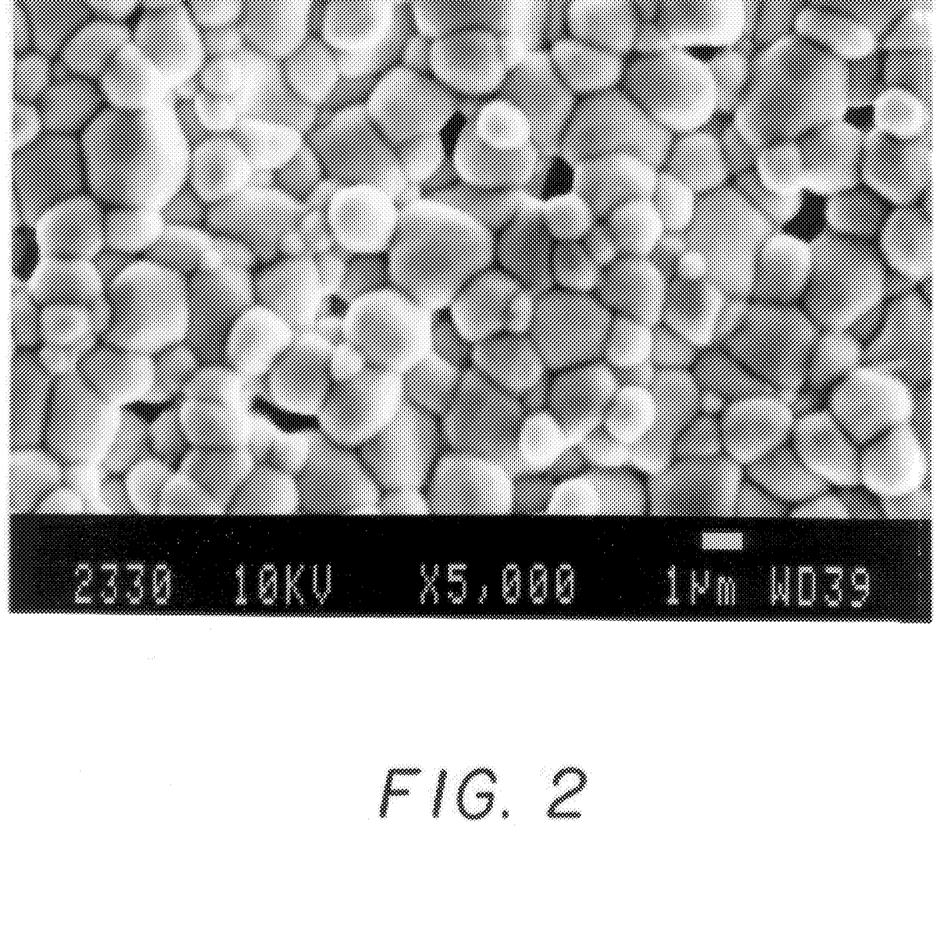
FIG. 2 is a photograph of a magnified view of the material in FIG. 1.

Sintered specimens analyzed by SEM showed evidence of liquid phase sintering in $(La,Ca)(Cr,V)O_3$. FIG. 1 shows an unpolished surface of $La_{0.76}Ca_{0.26}CrO_3$+2 at % V sintered at 1300° C. for 2 h. The glassy striations on the surface of the $(La,Ca)(Cr,V)O_3$ grains are typical of the liquid phase also found in the $(La,Ca)CrO_3$ system. Elemental analysis of the liquid phase showed the presence of Ca,V and Cr. After the grains coalesced and the pores filled in, excess liquid segregated out of the grains to the free surface. A magnified view of the same specimen in FIG. 2 shows that the $(La,Ca)(Cr,V)O_3$ grains have sintered to high density with 5–7 vol % porosity.

Figure 3A:
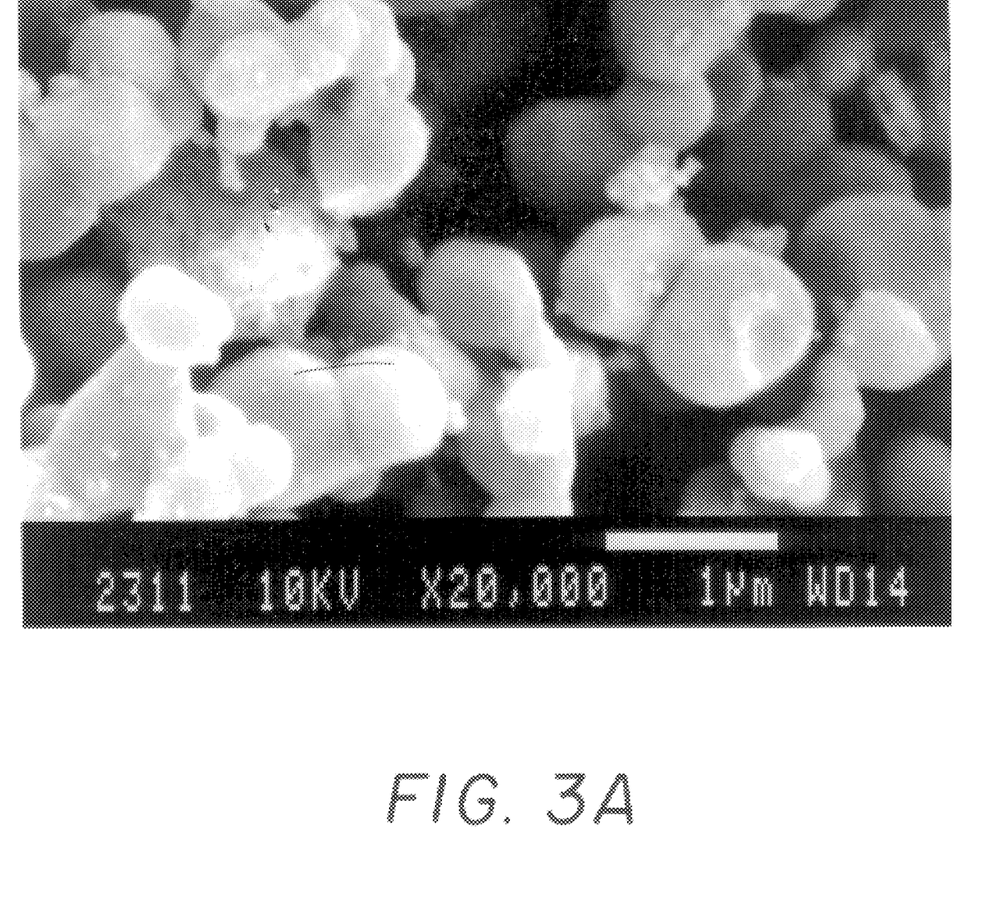
FIG. 3a is a photograph of a magnified view of LCC65 particles.
Figure 3B:
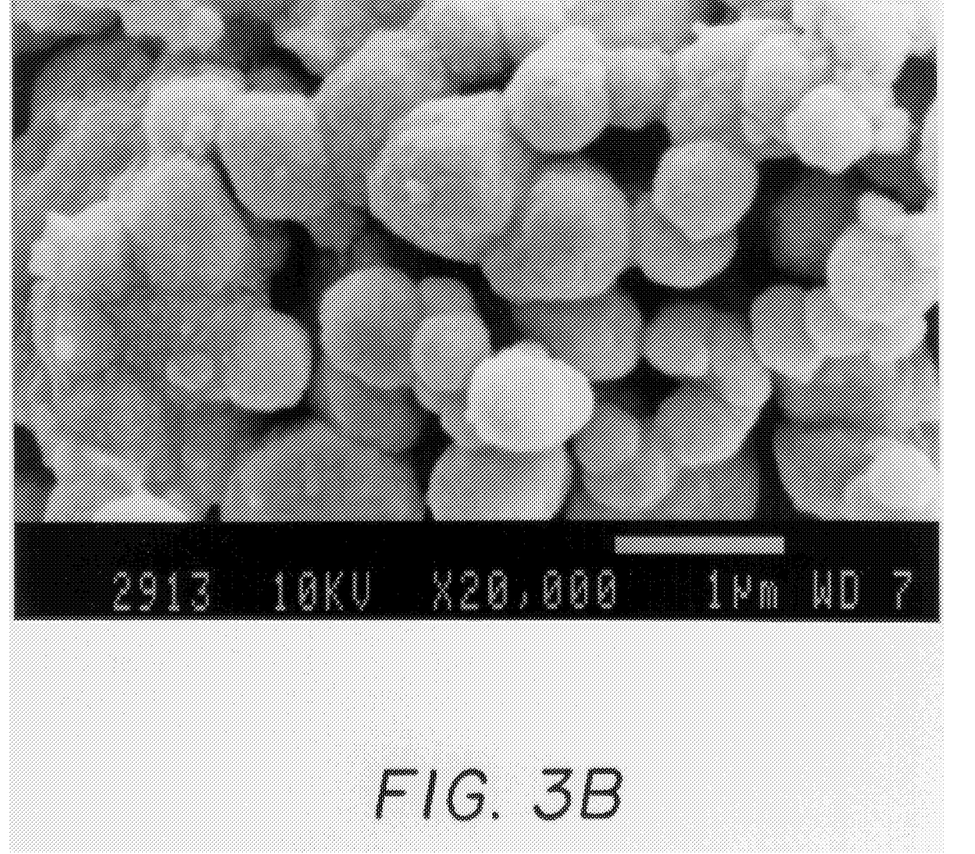
FIG. 3b is a photograph of a magnified view of the material of FIG. 3a after coating and calcination.

To investigate the nature of $VO_x$ coating, a microscopic study was made of LCC65 with and without the addition of the $VO_x$-citric acid solution. In this case the $VO_x$-citric acid solution was added to a stirred slurry of $(La,Ca)CrO_3$ in ethanol. FIG. 3a shows LCC65 particles (without V), calcined at 1200° C. for 2 h. The particle surfaces appear smooth with edges on the facets. FIG. 3b shows the same powder after it had been coated with the $VO_x$-citric acid solution and calcined at 650° C. to remove the organics. Here, the particle surfaces have a textured coating which is distributed throughout the bulk of the powder matric. Sintered bodies made from this powder revealed a uniform grain size as seen in FIG. 2.

(La,Sr) (Cr,V)O₃

Figure 4:
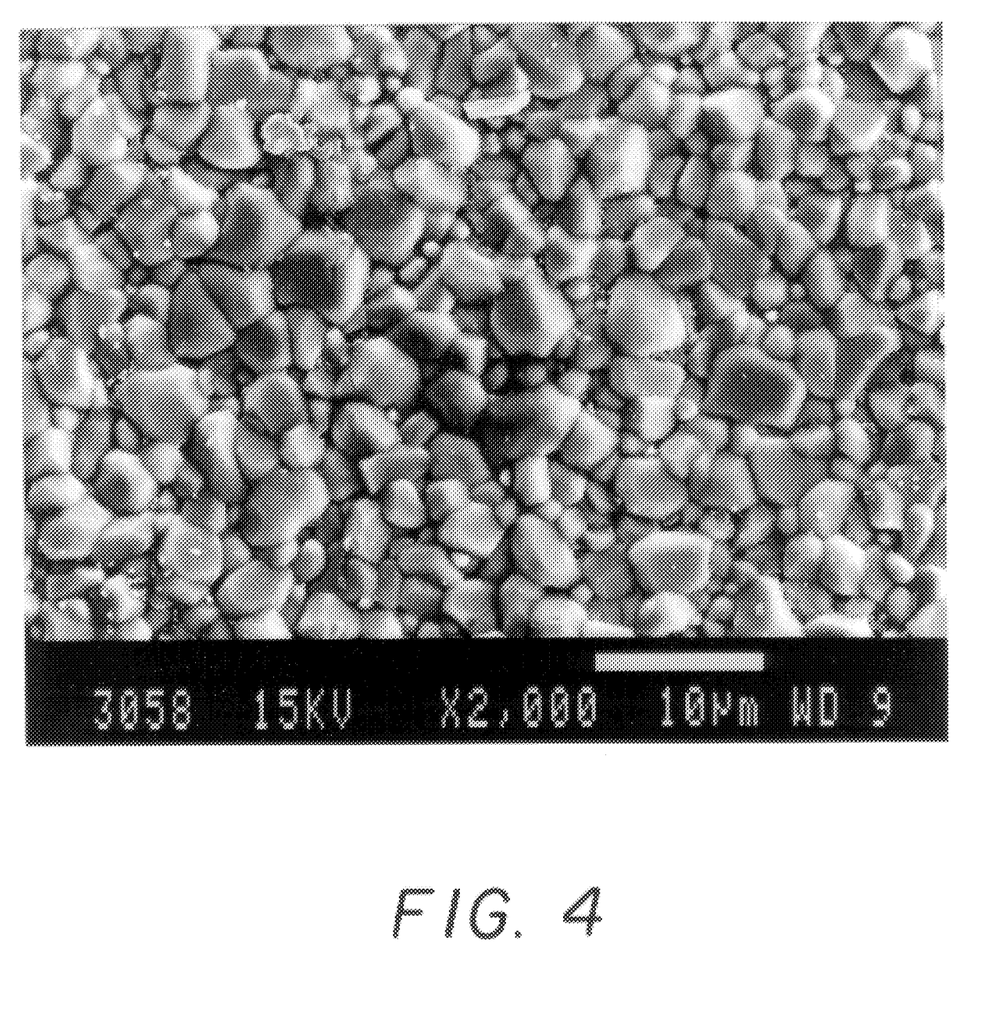
FIG. 4 is a photograph of an unpolished surface of a material according to the present invention.

Microscopic analysis of $(La,Sr)(Cr,V)O_3$ compositions showed uniform grain growth and high sintering density. FIG. 4 shows an unpolished surface of a pellet of $La_{0.8}Sr_{0.2}Cr_{0.97}V_{0.03}O_3$ (DC27), calcined at 1000° C./2 h and sintered at 1400° C./2 h. $SrCrO_4$ was identified by XRD (x-ray diffraction) as one of the a secondary phases forming in $(La,Sr)(Cr,V)O_3$, below 1000° C. Since the phase diagram of the $SrO—Cr_2O_3$ system, cf. T. Negas and R. S. Roth, J.Res.Nat.Bur.Stand.Sect.A,73 [4] (1969) 433.34, shows that $SrCrO_4$ melts between 1250°–1285° C., it is believed that a modification of this liquid phase also occurs in the (La,Sr)(Cr,V)$O_3$ system and acts as a sintering aid. Possible remnants of a liquid phase can be seen between the grains in FIG. 4. Microscopic analysis of a similar specimen sintered at 1450° C. for 2 h showed a molten phase on the free surface with an appearance similar to that found in the (La,Ca)(Cr,V)$O_3$ specimens.

Phase analysis

Figure 5:
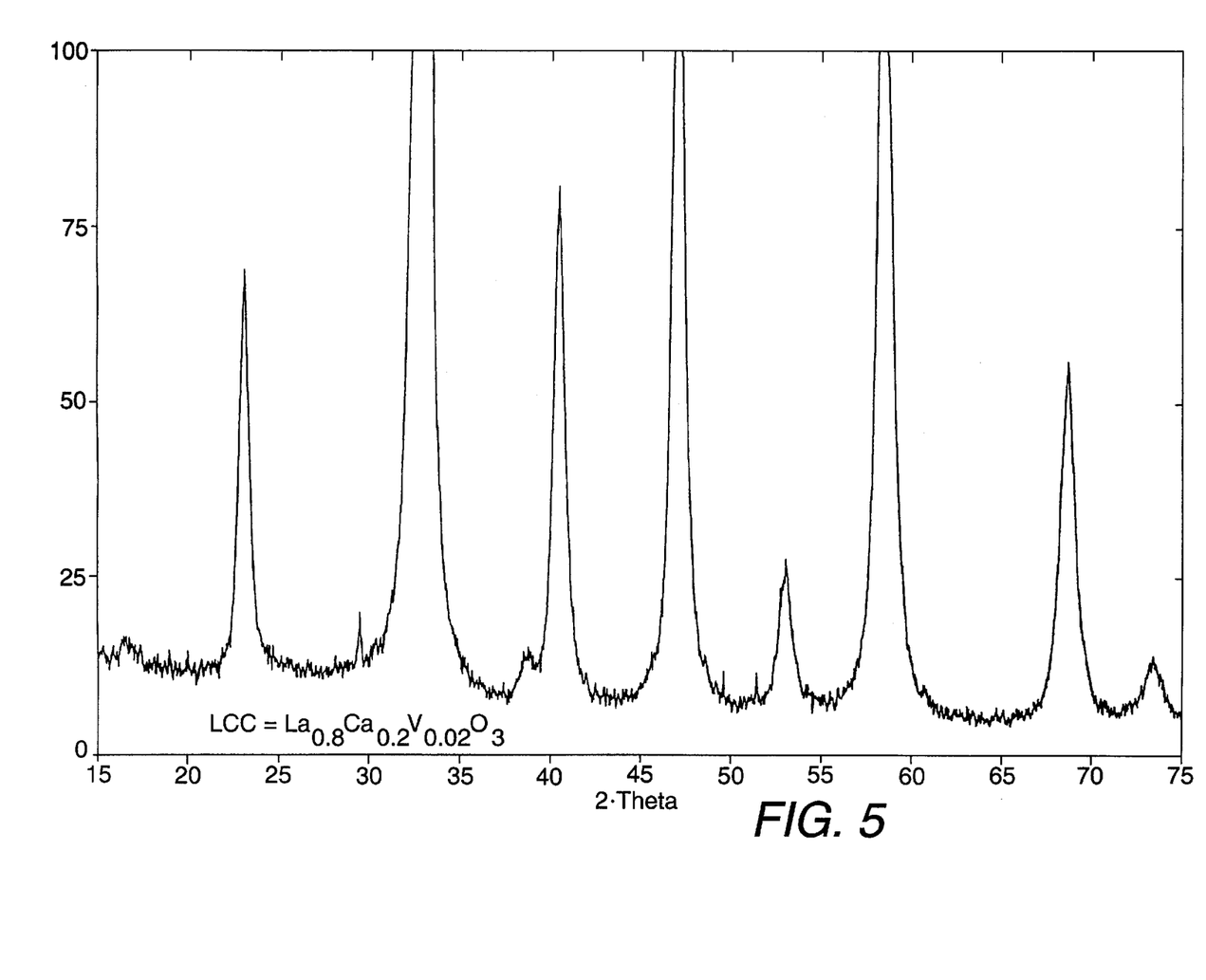
FIG. 5 is a graph of an x-ray diffraction pattern of a material according to the present invention.

X-ray diffraction was employed to identify secondary phases which exsolve from (La,M)(Cr,V)$O_3$ at various temperatures during annealing and sintering. Diffraction patterns of (La,M)(Cr,V)$O_3$ compositions, synthesized using the glycine process are characteristically single phase with broad peaks indicating submicron primary particle sizes. For example, FIG. 5 is a diffraction pattern of as-synthesized $La_{0.8}Sr_{0.2}Cr_{0.98}V_{0.02}O_3$. It is believed that the apparent high solubility for foreign ions in $LaCrO_3$ is caused by the high temperature of pyrolysis and rapid cooling of the resulting particles as they are discharged from the pyrolysis zone. The diffraction pattern of the as-synthesized powder changes according to temperature; when powders are heated above 400° C., the diffraction peaks sharpen and secondary phases appear according to the equilibrium solubility of foreign ions in the host matrix.

In the (La,M)(Cr,V)$O_3$ system, the secondary phases can ordinarily be identified between 20°–36°-2θ in the diffraction pattern. In both Sr and Ca doped (La,M)(Cr,V)$O_3$, either $LaVO_4$ or $LaCrO_4$ or a solid solution of both form as a secondary phase at temperatures below 700° C. The two compounds are isostructural, each having a monazite-type structure (space group: P2$_1$/n), and exhibit closely similar diffraction patterns, cf. $LaCrO_4$, JCPDS Card # 36-93, Joint Committee on Powder Diffraction Standards, 1601 Park Lane, Swarthmore, Pa. 19081 (1986) and $LaVO_4$, JCPDS Card # 25-427, Joint Committee on Powder Diffraction Standards, 1601 Park Lane, Swarthmore, Pa. 19081 (1975). Consequently, they are difficult to resolve from another using only XRD. But the present belief is that $LaVO_4$ is the phase formed because these diffraction peaks are not seen in compositions not containing V; and $LaVO_4$ is the most stable form of vanadates in air, cf. T. Nakamura, G. Petzow and L. Gaukler, *Mat.Res.Bull.*, 14 (1979) 649–659. In contrast, $LaCrO_4$ is relatively unstable in air under such conditions, cf. J. D. Carter, H. U. Anderson, M. G. Shumsky, "Structure and Phase Transformation of Lanthanum Chromate". Submitted for publication in the *J.Mat.Sci.* (1994).

Figure 6:
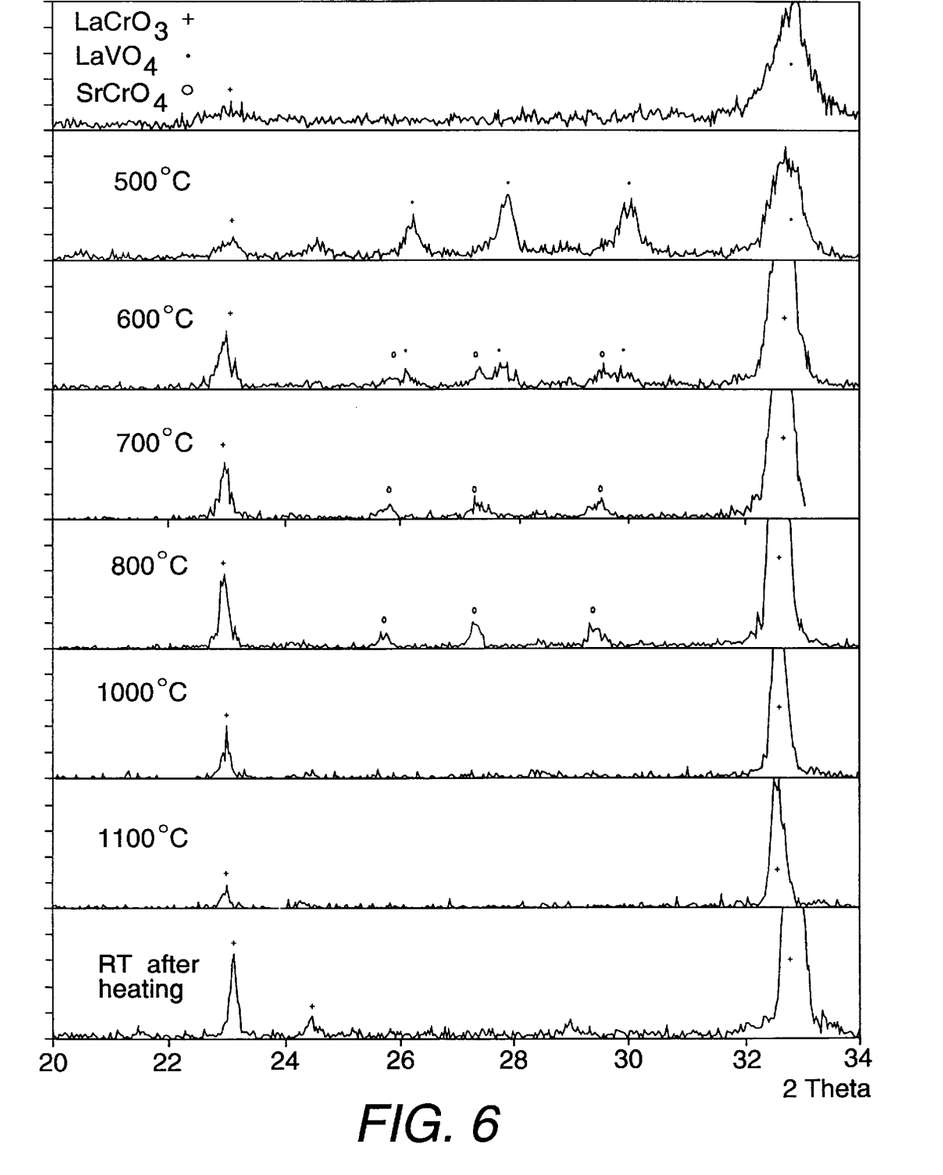
FIG. 6 is a series of graphs of a high temperature x-ray diffraction pattern of the material of the invention.

When (La,M)(Cr,V)$O_3$ compositions are heated above 700° C., the $LaVO_4$ disappears and either $CaCrO_4$ of $SrCrO_4$ takes its place as a secondary phase. FIG. 6 shows a high temperature XRD pattern of $La_{0.8}Sr_{0.2}Cr_{0.97}V_{0.03}O_3$ (DC27) as it is heated to 1100° C. and then cooled. The diffraction pattern of the as-synthesized powder shows broad peaks and a noisy background. No secondary phases are visible. At 500° C., the peak widths have narrowed and $LaVO_4$ peaks have become prominent. At 600° C. the intensity of the $LaVO_4$ peaks decrease by half and peaks from $SrCrO_4$ become apparent. The crystal structure of $SrCrO_4$ is also monazite-type, cf. $SrCrO_4$, JCPDS Card # 35-743, Joint Committee on Powder Diffraction Standards, 1601 Park Lane, Swarthmore, Pa. 19081 (1985), but the XRD patterns of $SrCrO_4$ and $LaVO_4$ are more distinct. The peak intensities of $SrCrO_4$ increase as the temperature is raised through 700° and 800° C., but at 1000° C. they disappear. This could be the result of the formation of a liquid phase or because $SrCrO_4$ has dissolved into the (La,Sr)(Cr,V)$O_3$ matrix. Preliminary trials of differential thermal analysis (DTA) of $La_{0.8}Sr_{0.2}Cr_{0.97}V_{0.03}O_3$ (DC33) gave no indication of melting taking place at this temperature, so it is believed that the $SrCrO_4$ dissolves into (La,Sr)(Cr,V)$O_3$ at this temperature for this composition.

Figure 7:
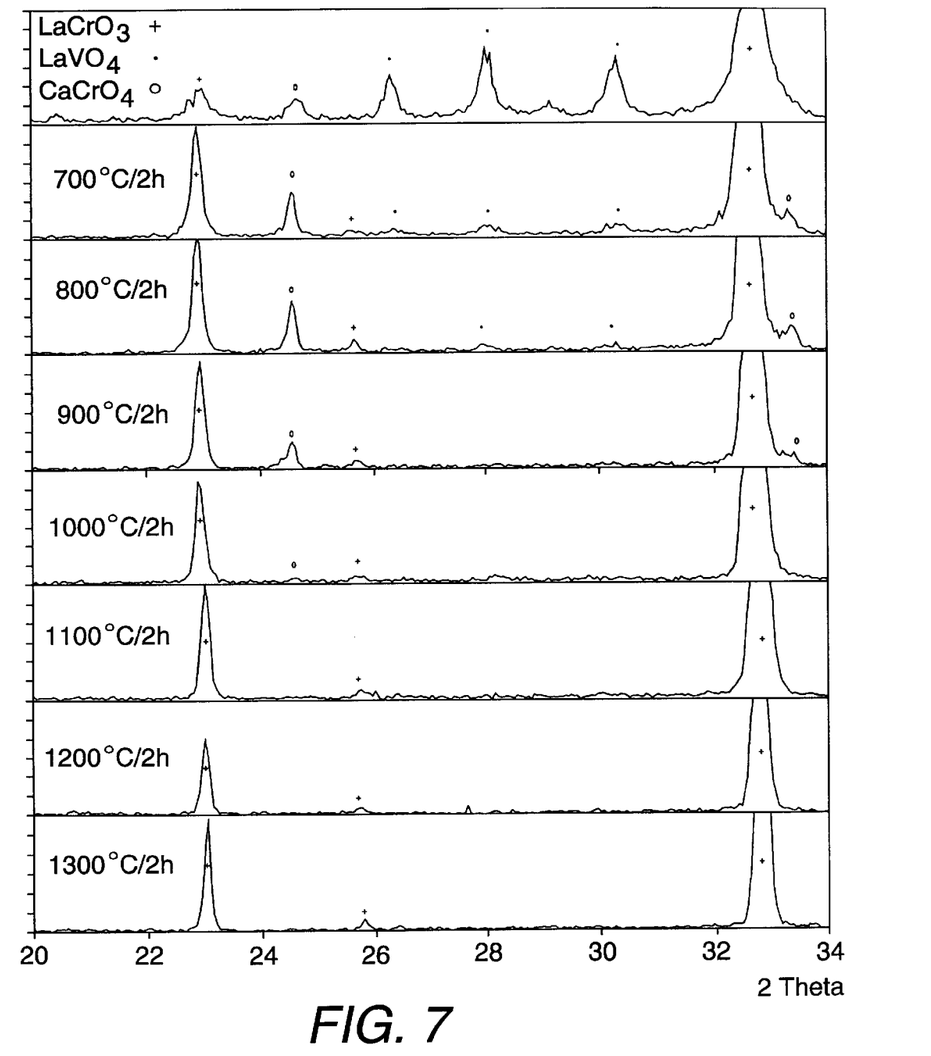
FIG. 7 is a series of graphs of a high temperature x-ray diffraction study for another material according to the invention.

A room temperature XRD study of annealed $La_{0.8}Ca_{0.2}Cr_{0.97}V_{0.03}O_3$ (DC32) specimens (as-synthesized [600° C.], 700°, 800°, 900°, ... 1300° C. for 2 h) showed similar results (FIG. 7). The as-synthesized powder shows the peaks from the perovskite and secondary peaks of $LaVO_4$. At 700° and 800° C. the intensity of the $LaVO_4$ peaks decrease and the $CaCrO_4$ phase becomes apparent. By 1000° C. the $CaCrO_4$ phase disappears and at 1100° C. only peaks from the perovskite phase are discernible. It is known from DTA analysis that $CaCrO_4$ melts near 1030° C.; and the resulting liquid phase has been shown to aid in sintering (La,Ca)Cr $O_3$, cf. J. D. Carter, M. M. Nasrallah, and H. U. Anderson, "Liquid Phase Behavior in Nonstoichiometric Calcium Doped Lanthanum Chromites". Submitted for publication in the *J.Mat.Sci.* (1994). The presence of V within the liquid phase is believed to enhance the sintering action of this liquid phase.

Electrical conductivity

Electrical conductivity measurements of (La,M)(Cr,V)$O_3$ in air and in reducing atmosphere indicate that the conductivity is relatively unaffected by the V doping. Table III shows the electrical conductivity values of (La,M)(Cr,V)$O_3$ and (La,Sr)$CrO_3$ compositions. The conductivities lie within the range of values found in the literature, cf. N. Sakai, T. Kawada, H. Yokokawa, M. Dokiya and T. Iwata, "Sinterability and Electrical Conductivity of Calcium-Doped Lantahnum Chromites", *J.Mater. Sci.* 25, 4531–4534 (1990), I. Yasuda and T. Hikita, *J. Electrochem. Soc.*, 140 [60] (1993) 1699–1704 and W. Schafer and R. Schmidberger, "Ca and Sr Doped $LaCrO_3$: Preparation, Properties and High Temperature Applications" pp. 1737–42 *High Tech Ceramics*. Edited by P. Vincenzini. (Amsterdam, Elsevier Science Publishers, 1987).

TABLE III

Electrical conductivities of (La,M)(Cr,V)$O_3$ at 1000° C.

| | Conductivity ($\Omega^{-1}$ cm$^{-1}$) | | |
|---|---|---|---|
| Composition | air -log 0.68 atm $O_2$ | -log 16 atm $O_2$ (10% $H_2$ in $N_2$) | Ref. |
| $La_{0.74}Ca_{0.36}CrO_3$ | 50 | 3 | 8 |
| $La_{0.76}Ca_{0.26}CrO_3$ + 2 at % V | 30 | 12 | this study |
| $La_{0.8}Ca_{0.2}CrO_3$ | 40 | 18 | 9 |
| $LA_{0.8}Ca_{0.2}Cr_{0.97}V_{0.03}O_3$ | 30 | 12 | this study |
| $La_{0.8}Sr_{0.2}CrO_3$ | 31 | — | 10 |
| $La_{0.8}Sr_{0.2}Cr_{0.97}V_{0.03}O_3$ | 30 | 5 | this study |

Continued studies on V doped (La,Ca)$CrO_3$ and (La,Sr)$CrO_3$ compositions show that sintering proceeds through a liquid phase sintering mechanism. Vanadium was seen to dissolve into the liquid phase and it is believed to enhance the ability of the Ca—Cr—O and the Sr—Cr—O liquid phase and it is believed to enhance the ability of the Ca—Cr—O and the Sr—Cr—O liquid phases to aid sintering. Electrical measurements showed that conductivities with respect to non V-doped compositions remained relatively constant.

Although other modifications and changes may be suggested by those skilled in the art, it is the intention of the inventor to embody within the patent warranted hereon all changes and modifications as reasonably and properly come within the scope of his contribution to the art.

I claim:

1. A method for making an electrode layer comprising the steps of:

providing a substrate having a surface;

depositing a layer of an electrode material on a said surface, said electrode material comprising $La_xCa_yCrO_3$, wherein $x+y \geqq 1$ and $y>0$;

adding an amount of vanadium to said electrode material before or after said depositing step to improve sinterability of the electrode material; and thereafter, sintering the layer to provide said electrode layer.

2. A method as defined in claim 1, wherein vanadium is added in an amount effective to provide from about 1 to about 10 mol % of vanadium in said electrode layer.

3. A method as defined in claim 1, wherein said vanadium is added to the electrode material prior to said depositing step.

4. A method as defined in claim 1, wherein said vanadium is added in the form of vanadium oxide or a $VO_\delta$-citric acid complex.

5. A method as defined in claim 1, wherein said vanadium is added to the electrode material after said depositing step by spraying a solution of a $VO_\delta$-citric acid complex onto the deposited electrode material prior to the sintering step.

6. A method as defined in claim 1, wherein in said sintering step the layer is sintered at a temperature of at least about 1300° C. for a period of at least about 2 hours.

7. A method as defined in claim 1, wherein the substrate comprises a solid state electrolyte of a solid oxide fuel cell.

8. A method as defined in claim 1, wherein the substrate comprises YSZ.

9. A method as defined in claim 1, wherein said substrate comprises a heating element.

10. A method as defined in claim 1, wherein said substrate comprises an oxygen sensor.

11. A method as defined in claim 1, wherein said electrode material is deposited in a layer in the form of a powder slurry.

12. A method as defined in claim 1, wherein said electrode material comprises $La_{0.8}Ca_{0.2}Cr_{O.98}V_{0.02}O_3$.

13. A method as defined in claim 1, wherein said electrode material comprises $La_{0.76}Ca_{0.24}CrV_{0.02}O_3$.

14. A method as defined in claim 1, wherein said electrode material comprises $La_{0.8}Ca_{0.2}Cr_{0.95}V_{0.10}O_3$.

* * * * *